(12) United States Patent
Yeager et al.

(10) Patent No.: US 6,323,241 B1
(45) Date of Patent: Nov. 27, 2001

(54) PROSTAGLANDIN COMPOSITIONS AND METHODS OF TREATMENT FOR MALE ERECTILE DYSFUNCTION

(75) Inventors: James L. Yeager, Deerfield, IL (US); Nadir Buyuktimkin; Servet Buyuktimkin, both of Lawrence, KS (US)

(73) Assignee: NexMed (Holdings) Inc., Robbinsville, NJ (US)

( * ) Notice: Subject to any disclaimer, the term of this patent is extended or adjusted under 35 U.S.C. 154(b) by 0 days.

(21) Appl. No.: 09/480,738

(22) Filed: Jan. 10, 2000

(51) Int. Cl.$^7$ .................. A61K 31/19; A61K 31/557; A61K 31/50; A61K 31/495; A61K 47/00

(52) U.S. Cl. .................. 514/573; 514/254; 514/782; 514/785; 514/946; 514/947

(58) Field of Search .................. 514/573, 254, 514/782, 785, 946, 947

(56) References Cited

U.S. PATENT DOCUMENTS

| | | |
|---|---|---|
| 2,818,855 | 1/1958 | Miller et al. . |
| 4,127,118 | 11/1978 | Latorre . |
| 4,254,145 | 3/1981 | Birnbaum . |
| 4,311,707 | 1/1982 | Birnbaum et al. . |
| 4,801,587 | 1/1989 | Voss et al. . |
| 4,980,378 | 12/1990 | Wong et al. . |
| 5,242,391 | 9/1993 | Place et al. . |
| 5,256,652 | 10/1993 | El-Rashidy . |
| 5,380,760 | 1/1995 | Wendel et al. . |
| 5,820,587 | 10/1998 | Place . |
| 5,843,961 | 12/1998 | Kock et al. . |
| 6,046,244 * | 4/2000 | Buyuktimkin et al. ............... 514/785 |
| 6,102,849 | 8/2000 | Hakac . |

FOREIGN PATENT DOCUMENTS

| | | |
|---|---|---|
| 0 357 581 | 3/1990 | (EP) . |
| 1 367 550 | 9/1974 | (GB) . |
| WO 91/16021 | 10/1991 | (WO) . |
| WO 99/65303 | 12/1999 | (WO) . |
| WO 00/33825 | 6/2000 | (WO) . |
| WO 00/69469 | 11/2000 | (WO) . |

OTHER PUBLICATIONS

Droller, M. J. et al. Impotence. Consensus Development Conference Statement, National Institutes of Health *JAMA* vol. 270, No. 1, pp. 83–90 (1993).

Murray, F. T. et al., Evaluation and Treatment of Erectile Dysfunction, *Amer. J. Medical Sci.* 309: 99–109 (1995).

O'Keefe, M., et al., Assessment and Treatment of Impotence, *Medical Clinics of North America* 79: 415–434 (1995).

Vickers, M. A., et al., Diagnosis and Treatment of Psychogenic Erectile Dysfunction in a Urological Setting: Outcomes of 18 Consecutive Patients. *J. Urology* 149: 1258–1261 (1993).

Padma–Nathan, H., et al., Treatment of Men with Erectile Dysfunction with Transurethral Alprostadil, *N. Engl. J. Med.*, 336: 1–7 (1997), see especially FIG. 1.

Peterson, C.A., et al., Erectile Response to Transurethral Alprostadil, Prazosin and Aprostadil–Prazosin Combinations., *J. Urol.*, 159: 1523–1528 (1998).

Porst, H., Transurethral Alprostadil with MUSE™ (medicated urethral system for erection) vs. intracavernous Alprostadil–a comparative study in 103 patients with erectile dysfunction, *Int. J. Impot. Res.*, 9: 187–192 (1997).

Benson, G., (see editorial comment), *J. Urol.*, 159: 1527–1528 (1998).

Büyüktimkin et al., Chemical Means of Transdermal Drug Permeation Enhancement in Transdermal and Topical Drug Delivery Systems, Ghosh T.K., Pfister W.R., Yum S.I. (Eds.), Interpharm Press Inc., Buffalo Grove, IL. (1997).

Pudney, J., and Anderson, D.J., Immunobiology of the human penile urethra, *Amer. J. Path.*, 147: 155–165 (1995).

Holstein, A.F., et al., Different epithelia in the distal human male urethra, *Cell Tiss. Res.* 264: 23–32 (1991).

Durso, D.F., Introduction, pp. 1–1 to 1–3 in Davidson, R. L. editor, *Handbook of Water–Soluble Gums & Resins*, McGraw–Hill, Inc., N.Y. (1980).

Seaman, J. K., Guar Gum, pp. 6–1 to 6–19 in Davidson, R. L. editor, *Handbook of Water–Soluble Gums & Resins*, McGraw–Hill, Inc., N.Y. (1980).

Seaman, J. K., Locust Bean Gum, pp. 14–1 to 14–16 in Davidson, R. L. editor, *Handbook of Water–Soluble Gums & Resins*, McGraw–Hill, Inc., N.Y. (1980).

Williams C. et al., Efficacy and safety of transurethral alprostadil therapy in men with erectile dysfunction, *Brit. J Urol.*, 81: 889–894 (1998).

*Physician's Desk Reference*, 51st Ed., pp. 2575–2576 (1997).

*The Merck Index*, 12th Ed., Merck & Co., N.J., pp. 1352–1354 (1996).

(List continued on next page.)

Primary Examiner—Marianne M. Cintins
Assistant Examiner—Donna Jagoe
(74) Attorney, Agent, or Firm—McDonnell Boehnen Hulbert & Berghoff

(57) ABSTRACT

The invention provides methods of treating erectile dysfunction comprising the step of placing within the fossa navicularis of the patient an effective erection-inducing amount of a prostaglandin $E_1$ composition of a semi-solid consistency. The composition comprises prostaglandin $E_1$, a penetration enhancer, a polysaccharide gum, a lipophilic compound, and an acidic buffer system. The penetration enhancer is an alkyl-2-(N,N-disubstituted amino)-alkanoate ester, an (N,N-disubstituted amino)-alkanol alkanoate, or a mixture of these. The lipophilic compound may be an aliphatic $C_1$ to $C_8$ alcohol, an aliphatic $C_8$ to $C_{30}$ ester, or a mixture of these. The composition includes a buffer system capable of providing a buffered pH value for said composition in the range of about 3 to about 7.4.

32 Claims, 4 Drawing Sheets

OTHER PUBLICATIONS

*Martindale The Extra Pharmacopoeia*, 28th Ed., London, The Pharmaceutical Press, p. 1353 (1982).

Kunelius, P., et al,m Intracavernous self–injection of Prostaglandin E1 in the treatment of Erectile Dysfunction. International Journal of Impotence Research 11:21–24 (1999).

Zecchi Orlandini, S., et al., Ultrastructure of Human Male Urethra. Archives of Andrology, 23:51–59 (1989).

Ishii, N., et al., Studies on Male Sexual Impotence Report II, The Japanese Journal of Urology, vol. 77, No. 9, pp. 954–961, (May 1986).

Hedlund H., et al., Contraction and Relaxation induced by some Porstanoids in Isolated Human Penile Erectile Tissue and Cavernous Artery, Journal of Urology, 154:1245–1250 (1986).

Gerber, G.S., et al., Pharmacological Erection Program Using Prostaglandin E1, Journal of Urology, 146:786–789 (1991).

Malloy, T.R., et al. Pharmacologic Treatment of Impotence, Urologic Clinics of North America, vol. 14, No. 2, pp. 297–305 (May 1987).

Wolfson B, et al., Intralurethral Prostaglandin E–2 Cream: A possible Alternative Treatment for Erectile Dysfunction, Urology, vol. 42, No. 1, pp. 73–75, Jul. 1993.

Catanzarite, V.A., et al., Prostaglandins: Mundane and Visionary applications, Contemporary OB/GYN, pp. 21–41 (Oct. 1987). Remington: Practice of the Science and Pharmacy, $19^{th}$ Edition Mack Publishing Company A.R. Gennaro (Ed.), pp. 410–412 (1995).

Chattarij, S.C. et al., Penetration Enhancer Classification in *Percutaneous Penetration Enhancers*, E.W. Smith, H.I. Maibach (Eds.). CRC, Press, Inc. pp. 5–20, (1995).

Büyüktimkin et al., Alkyl N,N–Disubstituted–Amino Acetates in Percutaneous Penetration Enhancers, E.W. Smith, H.I. Maibach (Eds). CRC, Press, Inc. pp. 91–102, (1995).

Tiefer, L., et al. Impotence: NIH Consensus Statement, vol. 10, No. 4, pp. 1–31 (1993).

International Search Report in PCT/US01/00852, dated May 29, 2001.

* cited by examiner

PROSTAGLANDIN COMPOSITIONS AND METHODS OF TREATMENT FOR MALE ERECTILE DYSFUNCTION

TECHNICAL FIELD OF THE INVENTION

This invention relates to the compositions and methods for treatment of erectile dysfunction, and more particularly to methods and pharmaceutical compositions for intranavicular administration of vasodilator medicaments to the fossa navicularis of a patient.

BACKGROUND OF THE INVENTION

The term "impotence" has been used to signify the inability of the male to attain and maintain erection of the penis sufficient to permit satisfactory sexual intercourse. The term "erectile dysfunction" has been suggested as a more precise term "to signify an inability of the male to achieve an erect penis as part of the overall multifaceted process of male sexual function." Droller, M. J. et al. Impotence. Consensus Development Conference Statement, National Institutes of Health (1993).

Erectile dysfunction may result from psychological causes (psychogenic erectile dysfunction) or organic causes or a combination of both. Organic causes include physiological, nervous, vascular and hormonal pathologies or a combination thereof.

The normal physiology of an erection involves nerve impulses which signal certain muscles to relax. These muscles, when contracted, restrict blood flow through arteries in the penis. When relaxed, the muscles permit a significant increase in blood flow. The increased blood flow engorges three groups of erectile tissue within the penis with blood and the penis becomes less flaccid. The engorged erectile tissue and the muscle structure of the penis depress adjacent veins, restricting the flow of blood out of the penis. The restriction of blood flow out of the penis increases and sustains the erection.

Deficiencies of some hormones, such as testosterone, or elevation of others, such as prolactin, can cause erectile dysfunction. Many drugs, such diuretics, antihypertensives, anticonvulsants, narcotics, alcohol, and psychotropic drugs may cause erectile dysfunction as a side effect. Murray, F. T. et al. Amer. J. Medical Sci. 309: 99–109 (1995).

Damage to nerves and blood vessels may also provide an organic cause for erectile dysfunction. Disease processes may involve several aspects. For example, diabetes, which causes damage to both nerves and blood vessels, can cause erectile dysfunction. A significant percent of all diabetic men will suffer from erectile dysfunction.

Methods proposed for the treatment of erectile dysfunction have included external devices, sex therapy, surgical implantation of internal prostheses, injection of drugs directly into the penis and topically applied medications. None of these approaches is entirely effective.

External devices include tourniquets (see U.S. Pat. No. 2,818,855) and externally applied vacuum erection aids. While some clinicians consider externally applied erection aids as a first option for treatment, some patients are unwilling to use such devices. O'Keefe, M., et al. Medical Clinics of North America 79: 415–434 (1995).

Symptomatic sex therapy was originally found to be effective by Masters and Johnson, but later studies have not shown as impressive results. Freudian therapy does not appear to patients to be an attractive alternative. Vickers, M. A., et al. J. Urology 149: 1258–1261 (1993).

Surgically implanted mechanical devices, such as hinged or solid rods and inflatable, spring driven or hydraulic prostheses have been used for some time.

The administration of erection effecting and enhancing drugs is taught in U.S. Pat. No. 4,127,118 to LaTorre. This patent teaches a method of treating male impotence by injecting into the penis an appropriate vasodilator, in particular, an adrenergic blocking agent or a smooth muscle relaxant to effect and enhance an erection.

More recently, U.S. Pat. No. 4,801,587 to Voss et al. teaches the application of an ointment to relieve impotence. The ointment consists of the vasodilators papaverine, hydralazine, sodium nitroprusside, phenoxybenzamine, or phentolamine and a carrier to assist absorption of the primary agent through the skin. U.S. Pat. No. 5,256,652 to El-Rashidy teaches the use of an aqueous topical composition of a vasodilator such as papaverine together with hydroxypropyl-β-cyclodextrin.

Prostaglandin $E_1$ is a derivative of prostanoic acid, a 20-carbon atom lipid acid, represented by the formula:

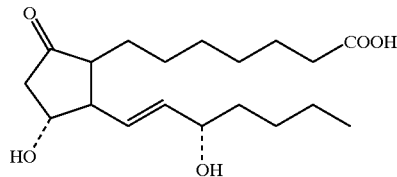

and is commercially available, e.g., from Chinoin Pharmaceutical and Chemical Works Ltd. (Budapest, Hungary) under the designation "Alprostadil USP," from Phamacia & Upjohn under the designation "Caverject" and from The Upjohn Company (Kalamazoo, Mich.) under the designation "Prostin VR."

Prostaglandin $E_1$ is a vasodilator useful to maintain open blood vessels and therefore, to treat peripheral vascular disease among other ailments. While the potential benefits from transdermal delivery of prostaglandin $E_1$ have long been recognized, prior efforts at developing a topical composition for prostaglandin delivery have not been fully successful.

In one commercially available form (MUSE®, Vivus, Menlo Park Calif.), alprostadil is administered in a pellet deposited in the urethra using an applicator with a hollow stem 3.2 cm in length and 3.5 mm in diameter (Padma-Nathan, H., et al., N. Engl. J. Med., 336: 1–7 (1997), see especially FIG. 1). In the home treatment portion of the Padma-Nathan et al. study, 32.7% of the patients (10.8% of administrations) receiving MUSE® complained of penile pain and 5.1% experienced minor urethral trauma, compared to 3.3% and 1.0%, respectively, of the patients receiving placebo. Frequency of report of these side effects has varied in subsequent studies: MUSE® producing penile pain in 17–23.6% of administrations, compared to 1.7% with placebo and minor urethral bleeding reported by 4.8% of patients (Peterson, Calif., et al., J. Urol., 159: 1523–1528 (1998)). In a study on a European population, 31% MUSE® patients reporting penile pain or burning sensations, 4.8% reporting urethral bleeding, and 2.9% reporting severe testicular pain (Porst, H., Int. J. Impot. Res., 9:187–192 (1997)). The percent of patients responding to MUSE® treatment, defined as having at least one erection considered sufficient for intercourse, has been reported to be 43% (Porst, 1997), 65.9% (Padma-Nathan et al., 1997) and 70.5% (Peterson et al., 1998), although published editorial comment has suggested that the percent of patients responding in the latter two studies is more properly reported as 30–40% (Benson, G., J. Urol., 159: 1527–1528 (1998).

In particular, there is presently no commercial source for a topical semi-solid formulation that is useful without a supporting device such as a patch, adhesive strip, and the like. For example, U.S. Pat. No. 5,380,760 to Wendel et al. is directed to a topical prostaglandin formulation that includes a pressure-sensitive, adhesive sheet of polyisobutylene.

Working alone most drugs, prostaglandin formulations included, do not sufficiently permeate the skin to provide drug concentration levels comparable to those obtained from other drug delivery routes. To overcome this problem, topical drug formulations typically include a skin penetration enhancer. Skin penetration enhancers also may be referred to as absorption enhancers, accelerants, adjuvants, solubilizers, sorption promoters, etc. Whatever the name, such agents serve to improve drug absorption across the skin. Ideal penetration enhancers not only increase drug flux across the skin, but do so without irritating, sensitizing, or damaging skin. Furthermore, ideal penetration enhancers should not adversely affect the physical qualities of the available dosage forms (e.g. cream or gel), or the cosmetic quality of the topical composition.

A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and B üyüktimkin et al., Chemical Means of Transdermal Drug Permeation Enhancement in Transdermal and Topical Drug Delivery Systems , Gosh T. K., Pfister W. R., Yum S. I. (Eds.), Interpharm Press Inc., Buffalo Grove, Ill. (1997).

A fully successful topical or transmucosal formulation for prostaglandin El has not yet been identified and commercially available. Unfortunately, prostaglandin $E_1$ is readily transformed by rearrangement and other reactions. This relative instability tends to complicate efforts at formulating composition for intranavicular delivery.

The present invention addresses these problems by providing a method and compositions for the intranavicular delivery of semi-solid, separation-resistant and chemically stable composition for the relatively rapid, sustained delivery of a vasodilator, preferably prostaglandin $E_1$.

SUMMARY OF THE INVENTION

The present invention provides methods and compositions for the treatment of erectile dysfunction by the intranavicular application of pharmaceutical compositions to the mammalian penis.

The invention provides methods of treating erectile dysfunction comprising the step of placing within the fossa navicularis of the patient an effective erection-inducing amount of a prostaglandin $E_1$ composition of a semi-solid consistency. The composition comprises a vasodilator, preferably prostaglandin $E_1$, a penetration enhancer, a polysaccharide gum, a lipophilic compound, and an acidic buffer system. The penetration enhancer is an alkyl-2-(N,N-disubstituted amino)-alkanoate ester, an (N,N-disubstituted amino)-alkanol alkanoate, or a mixture of these. The lipophilic compound may be an aliphatic $C_1$ to $C_8$ alcohol, an aliphatic $C_8$ to $C_{30}$ ester, or a mixture of these. The composition includes a buffer system capable of providing a buffered pH value for said composition in the range of about 3 to about 7.4.

Intranavicular placement of the vasodilator composition of the present invention, i.e., within in the fossa navicularis, provides a number of advantages over placing such compositions on the skin surface of the penis or depositing a composition within the more proximal "pars spongiosa" portion of the urethra. The fossa navicularis is a natural expanded chamber suitably adapted to receive and retain semisolid medicaments. A semi-solid medicament, such as the composition of the present invention, when placed in the fossa has higher impedance to flow at narrowed exits of this space, the meatus and the urethra. The impedance to flow is proportional to the product of the cross sectional area of the path and the path length.

The lining of the fossa navicularis is a non-keratinized stratified squamous epithelium, thereby providing for enhanced permeablility compared to the keratinized epithelium of the surface skin of the outside of the penis.

The use of a short applicator that has a tip that ends within the anatomical limits of the fossa navicularis is less invasive than threading a longer applicator several centimeters up (or proximal) into the penile urethra proper. Preferably, the applicator comprises a reservoir containing an erection inducing amount of a semi-solid prostaglandin E1 composition. More preferably, the applicator is a single use device and contains a single dose of the semi-solid prostaglandin $E_1$ composition. The applicator is typically packed with instructions for use placed on all or some of the following; on the package containing the applicator, in a package insert and on the outside surface of the applicator itself.

The high glycogen content and bacterial flora within the fossa navicularis provides a naturally lower pH within the space, so that lower pH compositions that provide for high solubility of prostaglandin E1 can be more easily tolerated without excessive irritation of the tissues.

The fossa navicularis is also a more immunologically protected site than the adjacent pars spongiosa region of the penile urethra proper. Placing the tip of an applicator within the anatomical limits of the fossa navicularis thus presents less of a risk of circumventing the natural barriers to disease by artificially transporting contaminants, e.g., from the surface of the penis, directly into the penile urethra proper.

A pharmaceutical composition suitable for intranavicular application comprises prostaglandin $E_1$, a penetration enhancer, a polysaccharide gum, a lipophilic compound, and an acidic buffer system. The penetration enhancer is an alkyl-2-(N,N-disubstituted amino)-alkanoate ester, an (N,N-disubstituted amino)-alkanol alkanoate, or a mixture of these. The lipophilic compound may be an aliphatic $C_1$ to $C_8$ alcohol, an aliphatic $C_8$ to $C_{30}$ ester, or a mixture of these. The composition includes a buffer system capable of providing a buffered pH value for said composition in the range of about 3 to about 7.4. If desired, stabilizers, preservatives and emulsifiers may be included.

Compositions of the present invention can take the form of a semi-solid suitable for intranavicular application. In use as a intranavicular agent, these compositions exhibit relatively high prostaglandin penetration and bioavailability without requiring a wasteful overloading prostaglandin concentration. The composition further exhibit reduced irritation, sensitivity and damage of local tissues. In a preferred embodiment, the compositions are delivered to the fossa navicularis using an suitable single dose applicator.

Other and further aims, purposes, features, advantages, embodiments and the like will be apparent to those skilled in the art from the present specification and the appended claims.

DETAILED DESCRIPTION OF THE PREFERRED EMBODIMENTS

It has been unexpectedly found that that a semi-solid prostaglandin $E_1$ composition suitable for the treatment of erectile dysfunction can be placed advantageously in a natural enlarged space immediately proximal to the penile meatus, the fossa navicularis.

The fossa navicularis provides a restricted site that is ideally suited for the application of pharmaceutical compositions. The space is lined by a non-keratinized stratified squamous epithelium and is thereby distinguished from the surface skin covering the glans and the rest of the penis and from the stratified columnar epithelium of the lining of the urethra proper. It has been found that the administration of the composition of the present invention in the fossa navicularis has unexpectedly high efficacy and low incidence of local side effects.

The fossa navicularis provides a natural space adaptable to the application and retention of pharmaceutical compositions. A semi-solid medicament, such as the composition of the present invention, when placed in the fossa has higher impedance to flow at narrowed exits of this space, the meatus and the urethra. Thus, a semi-solid medication of suitably chosen viscosity is naturally retained within the fossa, facilitating the absorption of active agents such as vasodilators.

The fossa navicularis is part of the natural defense system that protects the body against infection. tissues. The fossa navicularis is a more immunologically protected site than the adjacent pars spongiosa region of the penile urethra proper. Depositing a semisolid medicament within the anatomical limits of the fossa navicularis thus does not circumvent the natural barriers to disease by artificially transporting contaminants, e.g., from the surface of the penis, directly into the penile urethra proper. As noted above, the fossa navicularis naturally supports a bacterial flora that maintains an acid pH.

Figure 1:
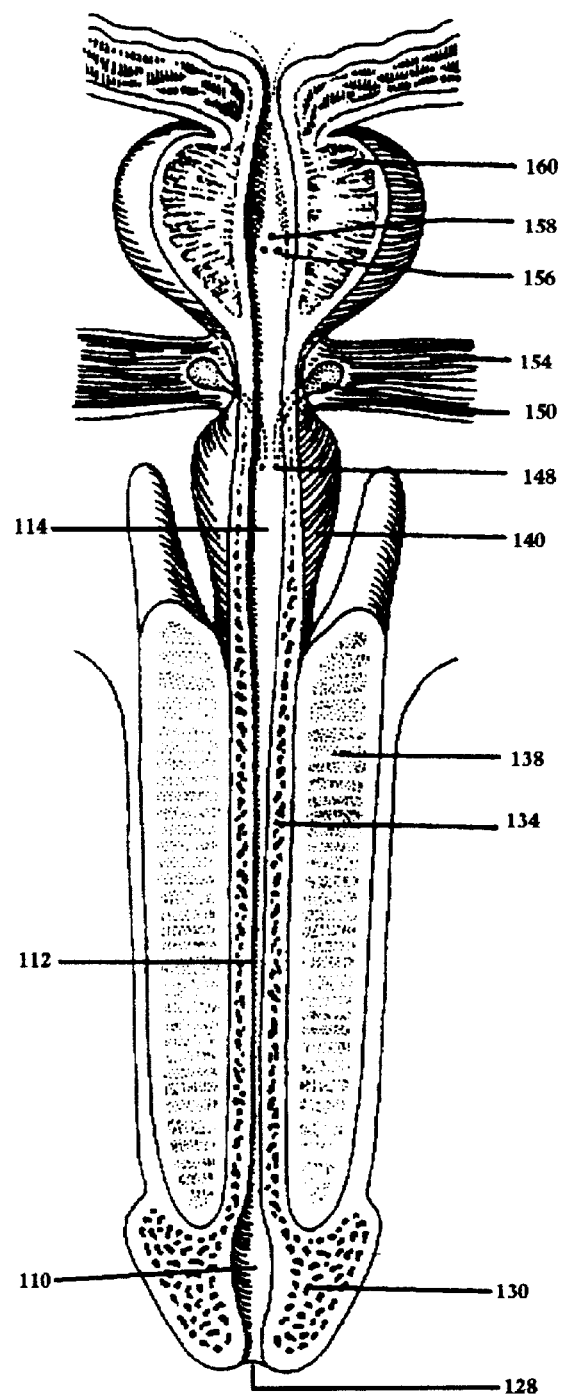
FIG. 1 is a diagram of the anatomical structure of the human penis in longitudinal section view.

Referring to FIG. 1, the basic structure of the human penis is illustrated. The fossa navicularis 110 is a natural enlargement of the lumen of the male urethra that extends distally to the urethral meatus 128 and proximally to the pendulous region of the urethra 112 (also termed "pars spongiosa" region of the urethra), the portion of the urethra that passes through the corpus spongiosum 134. The bulbar urethra 114 is proximal to the pendulous region of the urethra, and passes through the bulbospongiosus muscle 140. More proximally, the opening 148 in the wall of the urethra of the bulbourethral glands (Cowper's glands)can be seen. More proximally, the urethra passes through the prostate gland 160, where openings ejaculatory duct 156 and of the prostate utricle 158 are visible in wall of the urethra.

Figure 2:
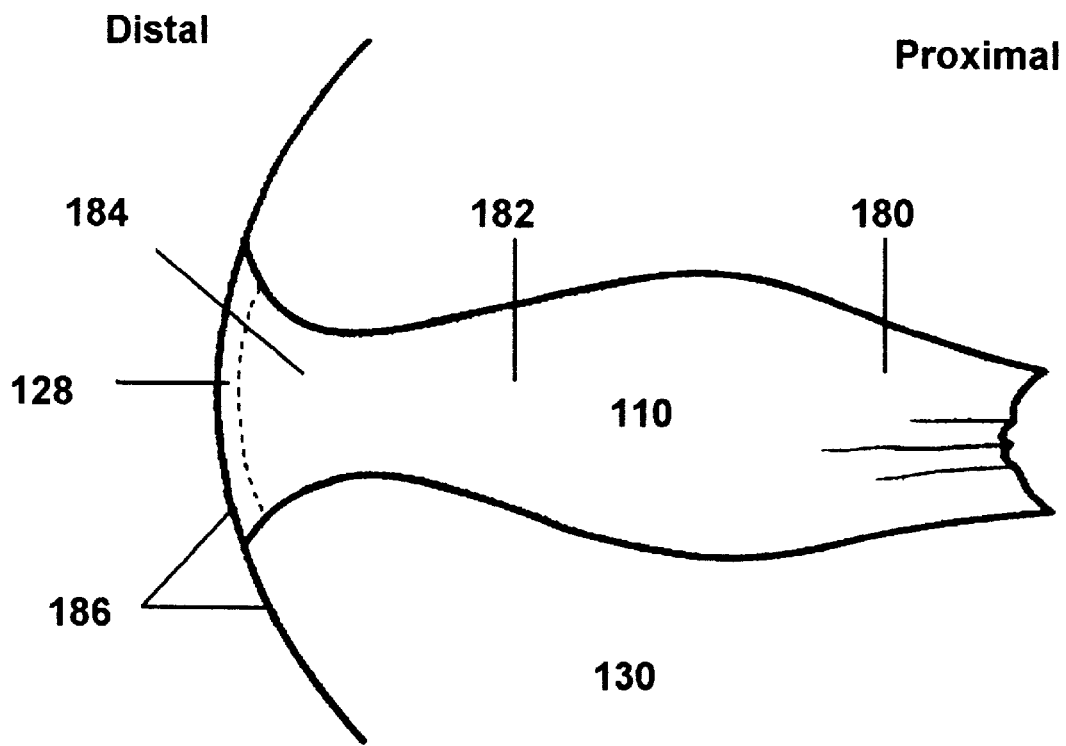
FIG. 2 is a diagram of the anatomical details of the distal portion of the human penis in longitudinal section view.

Referring to FIG. 2, the detailed structure of the fossa navicularis 110 is illustrated. The external opening of the urethral meatus 128 is the distal limit of the fossa navicularis. The external skin lo of the glans is covered by a keratinized stratified squamous epithelium 186 (Pudney, J., and Anderson, D. J., (1995) Immunobiology of the human penile urethra, Amer. J. Path., 147: 155–165) that is marked by proximally by a sharp transition (dashed line) to the nonkeratinized stratified squamous epithelium without glycogen 184 that is characteristic of the lining of the distal fossa navicularis.

The fossa navicularis widens proximally and the lining changes to a nonkeratinized stratified squamous epithelium with glycogen 182. The glycogen in this region is believed to support a bacterial flora that lowers the pH of the region and contributes to a natural defense against infection. Holstein, A. F., et al., (1991) Different epithelia in the distal human male urethra, Cell Tiss. Res. 264: 23–32. This nonkeratinized stratified squamous epithelium with glycogen is under hormonal control, and increases in extent under increased estrogen levels. (Holstein, et al., 1991. The proximal fossa navicularis narrows in width, and is lined by a stratified columnar epithelium 180.

The method of the present invention also provides a relatively non-invasive applicator. When used to place an effective erection-inducing amount of a prostaglandin E1 composition within the fossa navicularis, the tip of the applicator does not extend beyond the anatomical limits of the fossa navicularis. Preferably, the tip of the applicator does not extend into the penis more than about two centimeters beyond the metal opening, more preferably no more than about 2 centimeter, most preferably no more than about 0.5 centimeters. Preferably, the applicator comprises a reservoir containing an erection inducing amount of a semi-solid composition comprising at least one vasodilator, preferably a prostaglandin El composition. More preferably, the applicator is a single use device and contains a single dose of the semi-solid vasodilator composition. The applicator is typically packed with instructions for use placed on all or some of the following; on the package containing the applicator, in a package insert and on the outside surface of the applicator itself.

The pharmaceutical composition of the present invention comprises at least one vasodilator, preferably prostaglandin $E_1$, an alkyl (N,N-disubstituted amino) ester, a polysaccharide gum, a lipophilic compound, and an acid buffer system.

Suitable vasoactive agents include, but are not limited to: nitrates such as nitroglycerin, isosorbide dinitrate, erythrityl tetranitrate, amyl nitrate, sodium nitroprusside, molsidomine, linsidomine chlorhydrate ("SIN-1") and S-nitroso-N-acetyl-d,l-penicillamine ("SNAP"); amino acids such as L-arginine; long and short acting α-blockers such as phenoxybenzamine, dibenamine, doxazosin, terazosin, phentolamine, tolazoline, prazosin, trimazosin, alfuzosin, tamsulosin and indoramin; vasodilative natural herbal compositions and bioactive extracts thereof, such as gosyajinki-gan, *Satureja obovata*, bai-hua qian-hu, lipotab, saiboku-to, vinpocetine, *Gingko biloba*, bacopa, *Gynostemma pentaphyllum*, gypenosides, *Evodia rutaecarpa*, rutaecarpine, dehydroevodiamine, dan-shen, salviae miltiorrhizae radix, shosaikoto, Zizyphi fructus, ginseng and mixtures thereof (U.S. Pat. No. 6,007,824); ergot alkaloids such as ergotamine and ergotamine analogs, e.g., acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride and terguride; antihypertensive agents such as diazoxide, hydralazine and minoxidil; vasodilators such as nimodepine, pinacidil, cyclandelate, dipyridamole and isoxsuprine; chlorpromazine; haloperidol; yohimbine; trazodone; naturally occurring prostaglandins such as $PGE_1$, $PGA_1$, $PGB_1$, $PGF_{1\alpha}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_{3\alpha}$; semisynthetic or synthetic derivatives of natural prostaglandins, including carboprost tromethamine, dinoprost tromethamine, dinoprostone, lipoprost, gemeprost, metenoprost, sulprostone and tiaprost; and vasoactive intestinal peptides. Prazosin, prostaglandin $E_1$ and prostaglandin $E_2$ are particularly preferred vasoactive agents for use in conjunction with the present method. Additionally, simultaneous administration of two or more vasoactive agents may be desirable and may in some cases exhibit a synergistic effect. The combination of prazosin with prostaglandin $E_1$ has been found to be particularly advantageous in this regard; the latter drug appears to act a permeation enhancer for prazosin, i.e., it increases the rate at which prazosin permeates through the skin or mucosal tissue and enters the bloodstream.

Prostaglandin $E_1$ is well known to those skilled in the art. Reference may be had to various literature references for its pharmacological activities, side effects, and normal dosage ranges. See for example, Physician's Desk Reference, 51st Ed. (1997), The Merck Index, 12th Ed., Merck & Co., N.J. (1996), and Martindale The Extra Pharmacopoeia, 28th Ed., London, The Pharmaceutical Press (1982). Prostaglandin $E_1$ as well as other compounds referenced herein are intended to encompass pharmaceutically acceptable derivatives including physiologically compatible salts and ester derivatives thereof.

The quantity of prostaglandin $E_1$ in the pharmaceutical compositions of the present invention is a therapeutically effective amount and necessarily varies according to the desired dose, the dosage form (e.g., suppository or topical), and the particular form of prostaglandin $E_1$ used. The term "prostaglandin" as used generically herein refers to the prostaglandin free acid and pharmaceutically acceptable derivatives thereof, including $PGE_1$, pharmaceutically acceptable salts and lower alkyl esters thereof (the term "lower alkyl" as used herein means straight chain or branched chain alkyl containing one to four carbon atoms). The composition generally contains between 0.05 percent to 1 percent prostaglandin $E_1$, preferably from 0.1 percent to 0.5 percent, based on the total weight of the composition.

An important component of the present invention is the penetration enhancer. The penetration enhancer is an alkyl-2-(N,N-disubstituted amino)-alkanoate, an (N,N-disubstituted amino)-alkanol alkanoate, or a mixture of these. For convenient reference, alkyl-2-(N,N-disubstituted amino)-alkanoates and (N,N-disubstituted amino)-alkanol alkanoates can be grouped together under the label alkyl (N,N-disubstituted amino) esters.

Alkyl-2-(N,N-disubstituted amino)-alkanoates suitable for the present invention can be represented as follows:

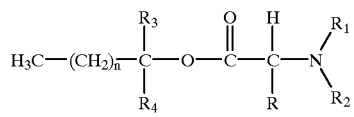

wherein n is an integer having a value in the range of about 4 to about 18; R is a member of the group consisting of hydrogen, $C_1$ to $C_7$ alkyl, benzyl and phenyl; $R_1$ and $R_2$ are members of the group consisting of hydrogen and $C_1$ to $C_7$ alkyl; and $R_3$ and $R_4$ are members of the group consisting of hydrogen, methyl and ethyl.

Preferred alkyl (N,N-disubstituted amino)-alkanoates are $C_4$ to $C_{18}$ alkyl (N,N-disubstituted amino)-acetates and $C_4$ to $C_{18}$ alkyl (N,N-disubstituted amino)-propionates and pharmaceutically acceptable salts and derivatives thereof. Exemplary specific alkyl-2-(N,N-disubstituted amino)-alkanoates include dodecyl 2-(N,N dimethylamino)-propionate (DDAIP);

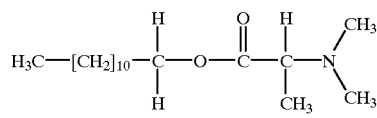

and dodecyl 2-(N,N-dimethylamino)-acetate (DDAA);

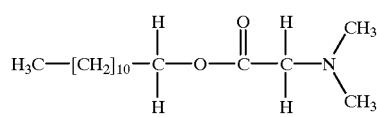

Alkyl-2-(N,N-disubstituted amino)-alkanoates are known. For example, dodecyl 2-(N,N-dimethylamino)-propionate (DDAIP) is available from Steroids, Ltd. (Chicago, Ill). In addition, alkyl-2-(N,N-disubstituted amino)-alkanoates can be synthesized from more readily available compounds as described in U.S. Pat. No. 4,980,378 to Wong et al., which is incorporated herein by reference to the extent that it is not inconsistent. As described therein, alkyl-2-(N,N-disubstituted amino)-alkanoates are readily prepared via a two-step synthesis. In the first step, long chain alkyl chloroacetates are prepared by reaction of the corresponding long chain alkanols with chloromethyl chloroformate or the like in the presence of an appropriate base such as triethylamine, typically in a suitable solvent such as chloroform. The reaction can be depicted as follows:

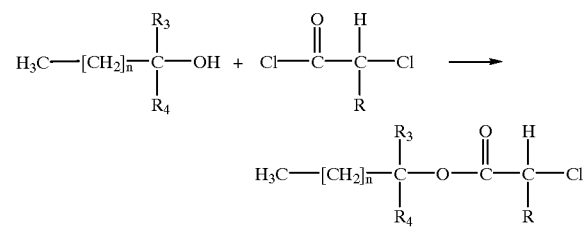

wherein R, $R_3$, $R_4$ and n are defined as above. The reaction temperature may be selected from about 10 degrees Celsius to about 200 degrees Celsius or reflux, with room temperature being preferred. The use of a solvent is optional. If a solvent is used, a wide variety of organic solvents may be selected. Choice of a base is likewise not critical. Preferred bases include tertiary amines such as triethylamine, pyridine and the like. Reaction time generally extends from about one hour to three days.

In the second step, the long chain alkyl chloroacetate is condensed with an appropriate amine according to the scheme:

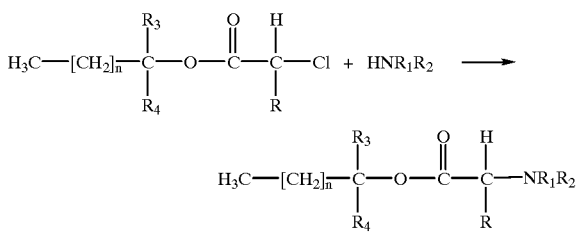

wherein n, R, $R_1$, $R_2$, $R_3$ and $R_4$ are defined as before. Excess amine reactant is typically used as the base and the reaction is conveniently conducted in a suitable solvent such as ether. This second step is preferably run at room temperature, although temperature may vary. Reaction time usually varies from about one hour to several days. Conventional purification techniques can be applied to ready the resulting ester for use in a pharmaceutical compound.

Suitable (N,N-disubstituted amino)-alkanol alkanoates can be represented by the formula:

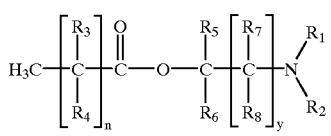

wherein n is an integer having a value in the range of about 5 to about 18; y is an integer having a value in the range of 0 to about 5; and $R_1$, $R_2$, $R_3$, $R_4$, $R_5$, $R_6$, and $R_7$ are members of the group consisting of hydrogen, $C_1$ to $C_8$ alkyl, and $C_1$ to $C_8$ aryl; and $R_8$ is a member of the group consisting of hydrogen, hydroxyl, $C_1$ to $C_8$ alkyl, and $C_1$ to $C_8$ aryl.

Preferred (N,N-disubstituted amino)-alkanol alkanoates are $C_5$ to $C_{18}$ carboxylic acid esters. Exemplary specific (N,N-disubstituted amino)-alkanol alkanoates include 1-(N, N-dimethylamino)-2-propanol dodecanoate (DAIPD);

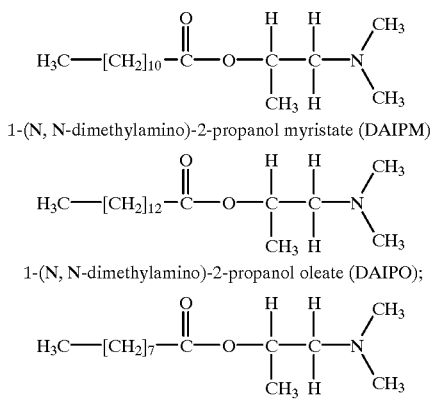

1-(N, N-dimethylamino)-2-propanol myristate (DAIPM)

1-(N, N-dimethylamino)-2-propanol oleate (DAIPO);

The (N,N-disubstituted amino)-alkanol alkanoates are readily prepared by reacting the corresponding aminoalkinol with lauroyl chloride in the presence of triethylamine. A solvent such as chloroform is optional but preferred. For example, 1-(N,N-dimethylamino)-2-propanol can be reacted with lauroyl chloride in chloroform and in the presence of triethylamine to form 1-(N,N-dimethylamino)-2-propanol dodecanoate (DAIPD).

Among the suitable penetration enhancers for the present invention DDAIP is generally preferred.

The penetration enhancer is present in an amount sufficient to enhance the penetration of the prostaglandin $E_1$. The specific amount varies necessarily according to the desired release rate and the specific form of prostaglandin $E_1$ used. Generally, this amount ranges from about 0.5 percent to about 10 percent, based on the total weight of the composition. Preferably, the penetration enhancer is about 5 weight percent of the composition.

Natural and modified polysaccharide gums are also an important ingredient to the present composition. Suitable representative gums are those in the nattural and modified galactomannan gum category. A galactomannan gum is a carbohydrate polymer containing D-galactose and D-mannose units, or other derivatives of such a polymer. There is a relatively large number of galactomannans, which vary in composition depending on their origin. The galactomannan gum is characterized by a linear structure of β-D-mannopyranosyl units linked (1→4). Single membered α-D-manopyranosyl units, linked (1→6) with the main chain, are present as side branches. Galactomannan gums include guar gum, which is the pulverized endosperm of the seed of either of two leguminous plants (*Cyamposis tetragonalobus* and psoraloids) and locust bean gum, which is found in the endosperm of the seeds of the carobtree (ceratonia siliqua). Locust bean gum is preferred for the present invention.

Suitable modified polysaccharide gums include ethers of natural or substituted polysaccharide gums, such as carboxymethyl ethers, ethylene glycol ethers and propylene glycol ethers. An exemplary substituted polysaccharide gum is methylcellulose.

Other suitable representative gums include agar gum, carrageenan gum, ghatti gum, karaya gum, rhamsan gum and xanthan gum. The composition of the present invention may contain a mixture of various gums, or mixture of gums and acidic polymers.

Gums, and galactomannan gums in particular, are well-known materials. See for instance, Industrial Gums: Polysaccharides & Their Derivatives, Whistler R. L. and BeMiller J. N. (eds.), 3rd Ed. Academic Press (1992) and Davidson R. L., Handbook of Water-Soluble Gums & Resins, McGraw-Hill, Inc., N.Y. (1980). Most gums are commercially available in various forms, commonly a powder, and ready for use in foods and topical compositions. For example, locust bean gum in powdered form is available from Tic Gums Inc. (Belcam, Md.).

The polysaccharide gums are represent in the range from about 0.5 percent to about 5 percent, based on the total weight of the composition, with the preferred range being from 0.5 percent to 2 percent. Illustrative compositions are given in the examples, below.

An optional alternative to the polysaccharide gum is a polyacrylic acid polymer. A common variety of polyacrylic acid polymer is known generically as "carbomer." Carbomer is polyacrylic acid polymers lightly cross-linked with polyalkenyl polyether. It is commercially available from the B. F. Goodrich Company (Akron, Ohio.) under the designation "CARBOPOL™." A particularly preferred variety of carbomer is that designated as "CARBOPOL 940."

Other polyacrylic acid polymers suitable for use in practicing this invention are those commercially available under the designations "Pemulen™" (B. F. Goodrich Company) and "POLYCARBOPHIL™" (A. H. Robbins, Richmond, Va.). The Pemulen™ polymers are copolymers of $C_{10}$ to $C_{30}$ alkyl acrylates and one or more monomers of acrylic acid, methacrylic acid or one of their simple esters crosslinked with an allyl ether of sucrose or an allyl ether of pentaerythritol. The POLYCARBOPHIL™ enhancer is a polyacrylic acid cross-linked with divinyl glycol.

Where polyacrylic acid polymers are present, they represent about 0.5 percent to about 5 percent of the composition, based on its total weight.

Another important component of the present invention is a lipophilic compound. The term lipophilic compound as used herein refers to an agent that is both lipophilic and hydrophilic. The $C_1$ to $C_8$ aliphatic alcohols, the $C_2$ to $C_{30}$ aliphatic esters, and their mixtures can serve as lipophilic compound. Illustrative suitable alcohols are ethanol, n-propanol and isopropanol, while suitable esters are ethyl acetate, butyl acetate, ethyl laurate, methyl propionate and isopropyl myristate. As used herein, the term "aliphatic alcohol" includes polyols such as glycerol, propylene glycol and polyethylene glycols. A mixture of alcohol and ester is preferred, and in particular, a mixture of ethanol and ethyl laurate myristate is most preferred.

The concentration of lipophilic compound required necessarily varies according to other factors such as the desired semi-solid consistency and the desired skin penetration promoting effects. The preferred topical composition contains lipophilic compound in the range of 7 percent to 40 percent by weight based on the total weight of the composition. Where a mixture of aliphatic alcohol and aliphatic ester are employed, the preferred amount of alcohol is in the range of 5 percent to 15 percent, while that of aliphatic ester is in the range from 2 percent to 15 percent (again based on the total weight of the composition).

An optional, but preferred, component of the present invention is an emulsifier. Although not a critical factor, a suitable emulsifier generally will exhibit a hydrophilic-lipophilic balance number greater than 10. Sucrose esters, and specifically sucrose stearate, can serve as emulsifiers for the topical composition of the present invention. Sucrose stearate is a well known emulsifier available from various commercial sources. When an emulsifier is used, sucrose stearate present up to about 2 percent, based on the total weight of the composition, is preferred. The preferred amount of sucrose stearate emulsifier can also be expressed as a weight ratio of emulsifier to polysaccharide gum. A ratio of 1 to 6 emulsifier to gum is preferred, and a ratio of 1 to 4 is most preferred to generate the desired semi-solid consistency and separation resistance.

The present invention includes an acid buffer system. Acid buffer systems serve to maintain or buffer the pH of compositions within a desired range. The term "buffer system" or "buffer" as used herein has reference to a solute agent or agents which, when in a water solution, stabilize such solution against a major change in pH (or hydrogen ion concentration or activity) when acids or bases are added thereto. Solute agent or agents which are thus responsible for a resistance to change in pH from a starting buffered pH value in the range indicated above are well known. While their are countless suitable buffers, potassium phosphate monohydrate has proven effective for compositions of the present invention.

The final pH value of the pharmaceutical composition of the present invention may vary within the physiologically compatible range. Necessarily, the final pH value is not irritating to human skin. Without violating this constraint, the pH may be selected to improve prostaglandin $E_1$ stability and to adjust consistency when required. With these factors accounted for, the preferred pH value is about 3.0 to about 7.4, more preferably about 3.0 to about 6.5, most preferably from about 3.5 to about 6.0.

The remaining component of the composition is water, which is necessarily purified. The composition contains water in the range of about 50 to about 90 percent, based on the total weight of the composition. The specific amount of water present is not critical, however, being adjustable to obtain the desired consistency and/or concentration of the other components.

Additionally, known transdermal penetration enhancers can also be added, if desired. Illustrative are dimethyl sulfoxide (DMSO), dimethyl acetamide (DMA), 2-pyrrolidone, N,N-diethyl-m-toluamide (DEET), 1-dodecylazacycloheptane-2-one (Azone™, a registered trademark of Nelson Research), N,N-dimethylformamide, N-methyl-2-pyrrolidone, calcium thioglycolate, oxazolidinone, dioxolane derivatives, laurocapram derivatives, and macrocyclic enhancers such as macrocyclic ketones.

Prostaglandin $E_1$ stabilizers, coloring agents, Theological agents, and preservatives can be added to the extent that they do not overly limit prostaglandin $E_1$ skin penetration or prevent the desired semi-solid consistency.

Contemplated dosage forms of the semi-solid pharmaceutical composition of the present invention are creams, gels, ointments, colloidal suspensions and the like, also including but not limited to compositions suitable for use with transdermal patches and like devices.

The ingredients listed above may be combined in any order and manner that produces a stable composition comprising a prostaglandin $E_1$ evenly dispersed throughout a semi-solid formulation. One available approach to preparing such compositions involves evenly dispersing the polysaccharide gum (or polyacrylic acid) in a premixed water/buffer solution and then thoroughly homogenizing (i.e. mixing) the resulting mixture, which will be labelled "Part A." When present, the emulsifier is added to the water/buffer solution before dispersing the polysaccharide gum. Any suitable method of adjusting the pH value of Part A to the desired level may be used, for example, by adding concentrated phosphoric acid or sodium hydroxide.

Separately, the prostaglandin $E_1$ is dissolved with agitation in the lipophilic compound, which itself may be a mixture of alcohols, esters, or alcohol with ester. Next, the penetration enhancer is added. Alternatively, when the lipophilic compound includes both an alcohol and an ester, the prostaglandin $E_1$ can be dissolved in the alcohol before adding the penetration enhancer followed by the ester. In either case, the resulting mixture will be labelled "Part B." The final step involves slow addition (.e.g. dropwise) of Part B into Part A under constant mixing.

The resulting topical composition, when compared to exhibits the advantageous properties described above, including improved prostaglandin $E_1$ permeation and bioavailability without drug overloading, reduced skin damage and related inflammation, and increased flexibility in design of dosage forms. These compositions can be used for prolonged treatment of peripheral vascular disease, male impotency and other disorders treated by prostaglandin $E_1$, while avoiding the low bioavailability and rapid chemical decomposition associated with other delivery methods. Application of prostaglandin $E_1$ in a topical composition of the present invention to the skin of a patient allows a predetermined amount of prostaglandin $E_1$ to be administered continuously to the patient and avoids undesirable effects present with a single or multiple administrations of larger dosages by injection. By maintaining a sustained dosage rate, the prostaglandin $E_1$ level in the patient's target tissue can be better maintained within the optimal therapeutic range.

The practice of the present invention is demonstrated in the following examples. These examples are meant to illustrate the invention rather than to limit its scope. Variations in the treating compositions which do not adversely affect the effectiveness of prostaglandin $E_1$ will be evident to one skilled in the art, and are within the scope of this invention.

For example, additional ingredients such as coloring agents, anti-microbial preservatives, emulsifiers, perfumes, prostaglandin $E_1$ stabilizers, and the like may be included in the compositions as long as the resulting composition retains desirable properties, as described above. Unless otherwise indicated, each composition is prepared by conventionally admixing the respective indicated components together.

EXAMPLE 1

Topical Prostaglandin $E_1$ Composition A

Composition A was prepared as follows. Part A was formed by dissolving 0.4 parts prostaglandin $E_1$ (Alprostadil USP) in 5 parts ethyl alcohol. Next, 5 parts dodecyl 2-(N, N-dimethylamino)-propionate were mixed into the alcohol-prostaglandin $E_1$ solution, followed by 5 parts ethyl laurate.

Part B was prepared starting from a pH 5.5 water/buffer solution. The water/buffer solution was prepared by adding sufficient potassium phosphate monohydried to purified water to create a 0.1 M solution. The pH of the water/buffer solution was adjusted to 5.5 with a strong base solution (1 N sodium hydroxide) and a strong acid (1 N phosphoric acid). The buffer solution represented about 80 parts of the total composition.

To the buffer solution, was added 0.5 parts ethyl laurate. Next, the locust bean gum (in powder form) was dispersed in the buffer solution and homogenized using a homogenizer. TABLE 1, below, contains a list of ingredients.

The resulting composition was a spreadable, semi-solid suitable for application to the skin without the need for supporting devices such as patches and adhesive strips. The composition was both homogenous in appearance and resistant to separation.

Composition A was evaluated for skin penetration using shed snake skin as a model barrier. Shed snake skin was obtained from the Animal Care Unit of the University of Kansas. With head and tail sections removed, the skin was randomly divided into test sections and then hydrated by soaking.

The samples were then evaluated using Franz-type Diffusion Cells (surface are 1.8 $cm^2$). Specifically, skin pieces were mounted on top of a receptor cell of a vertical diffusion cell assembly in which a small magnetic bar was inserted and filled with an isotonic buffer. A seal was placed on top of the skin section followed by a donor cell. The two cells were clamped together. Known amounts of the formulations were applied on the bottom of a small capped vial (weight 0.5 grams) which fits exactly to the donor cell to ensure uniform distribution. The vials were placed on the skin in the donor cell. To reduce the evaporation of the ingredients, the donor cell and vial were gently taped together with a water-resistant adhesive band. The cells were transferred to a stirred water bath (32 degrees Celsius). Samples were withdrawn from the cells each hour for four hours and analyzed for the concentration of prostaglandin $E_1$, with changes in concentration indicating the amount penetrating. Tests with multiple skin samples yielded data that were averaged.

For a discussion of the use of shed snake skin in the evaluation of drug penetration, see U.S. Pat. No. 4,771,004 to Higuchi, which is incorporated here by reference to the extent that it is not inconsistent.

The prostaglandin $E_1$ penetrated quickly at a relatively sustained rate for four hours. The results of the penetration study are presented in TABLE 2, below, and in FIG. 3.

EXAMPLE 2

Topical Prostaglandin $E_1$ Composition B

Composition B was prepared using the ingredients listed in TABLE 1, below. Composition B contained more prostaglandin $E_1$ than Composition A. Despite this increased drug loading, Composition B exhibited a similar semi-solid consistency and homogenous appearance. The penetration of prostaglandin $E_1$ was measured according to the technique described in Example 1. Composition B provided a relatively fast, sustained delivery of prostaglandin $E_1$. The results are presented in TABLE 2, below, and in FIG. 3.

EXAMPLE 3

Topical Prostaglandin $E_1$ Composition C

Composition C was prepared using the ingredients listed in TABLE 1, below. Composition B contained more prostaglandin $E_1$ than either Composition A or B. The increased drug loading had little or no effect on the consistency or appearance, which substantially matched that of Compositions A and B. The penetration of prostaglandin $E_1$ was again measured according to the technique described in Example 1. According to this test, Composition C also provided a relatively fast, sustained delivery of prostaglandin $E_1$.

The results are presented in TABLE 2, below, and in FIG. 3.

EXAMPLE 4

Topical Prostaglandin $E_1$ Composition D

Composition D was prepared using the ingredients listed in TABLE 1, below. The level of prostaglandin $E_1$ was again increased without substantially affecting the favorable consistency and separation resistance. The penetration of prostaglandin $E_1$ was again measured according to the technique described in Example 1. The results are presented in TABLE 2, below, and in FIG. 3.

EXAMPLE 5

Topical Prostaglandin $E_1$ Composition E

Composition E was prepared using the ingredients listed in TABLE 1, below. To assess the repeatability of compositions according to the present invention, the recipe of Composition D was again applied for Composition E. Repeatability was substantially confirmed by Composition E's favorable, semi-solid consistency and separation resistance. The penetration of prostaglandin $E_1$ was again measured according to the technique described in Example 1. The prostaglandin $E_1$ delivery from Composition E was again relatively fast and sustained. The results are presented in TABLE 2, below, and in FIG. 3.

EXAMPLE 6

Topical Prostaglandin $E_1$ Composition F

The level of prostaglandin $E_1$ was again increased for Composition F. The specific ingredients are listed in TABLE 1. The favorable consistency and separation resistance was undiminished. The results of a penetration analysis are presented in TABLE 2, below, and in FIG. 3.

EXAMPLE 7

Topical Prostaglandin $E_1$ Composition G

Composition G was prepared using the ingredients listed in TABLE 1. For Composition G, the recipe of Composition F was repeated except that the ester component (ester laurate) was omitted and the level of ethanol was increased a corresponding amount. The resulting composition was also a spreadable, semi-solid having a homogenous appearance and resistance to separation. The results of a penetration analysis are presented in TABLE 2, below, and in FIG. 3. While still favorable, these results reflect the relative benefit to compositions of the present invention from a lipophilic compound that includes both an ester component and an alcohol component.

TABLE 1

Topical Prostaglandin $E_1$ Compositions

| Ingredient (wt %) | A | B | C | D | E | F | G |
|---|---|---|---|---|---|---|---|
| Part A: | | | | | | | |
| prehydrated locust bean gum | 3 | 3 | 3 | 3 | 3 | 3 | 3 |
| water/buffer (pH 5.5) | 81 | 81 | 81 | 81 | 81 | 81 | 81 |
| sucrose stearate | 0.5 | 0.5 | 0.5 | 0.5 | 0.5 | 0.5 | 0.5 |
| Part B: | | | | | | | |
| prostaglandin $E_1$ | 0.1 | 0.2 | 0.3 | 0.4 | 0.4 | 0.5 | 0.4 |
| DDAIP | 5 | 5 | 5 | 5 | 5 | 5 | 5 |
| ethanol | 5 | 5 | 5 | 5 | 5 | 5 | 10 |
| ethyl laurate | 5 | 5 | 5 | 5 | 5 | 5 | — |

EXAMPLE 8

Comparison of Penetration Profiles

TABLE 2 shows the cumulative amount of prostaglandin $E_1$ penetrating each hour for 4 hours for each example composition according to the present invention. These data demonstrate the ability of the present invention to delivery prostaglandin $E_1$ drugs transdermally.

Figure 3:
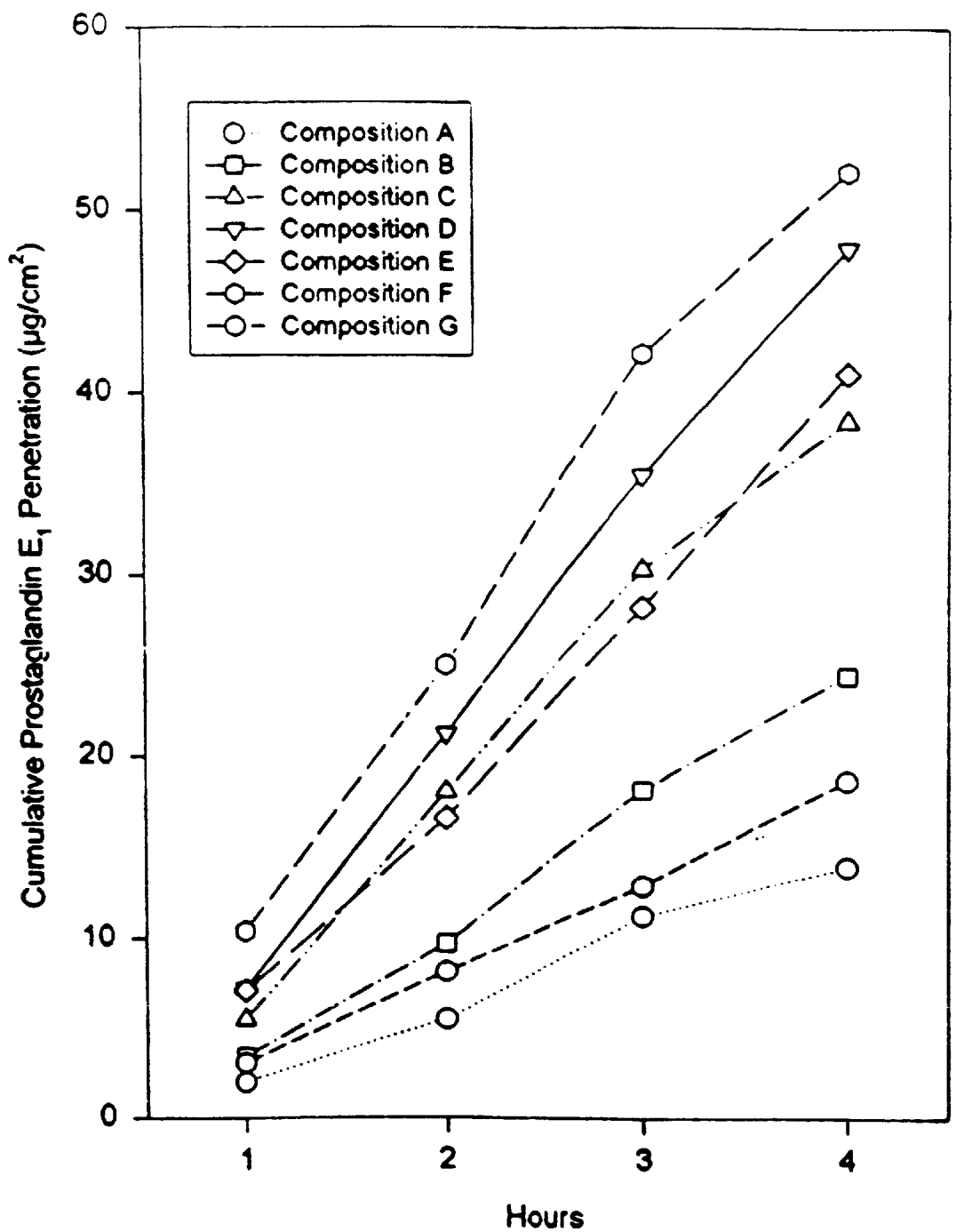
FIG. 3 is a graph of the cumulative prostaglandin $E_1$ penetration through shed snake skin of seven prostaglandin $E_1$ compositions prepared according to the present invention.
Figure 4:
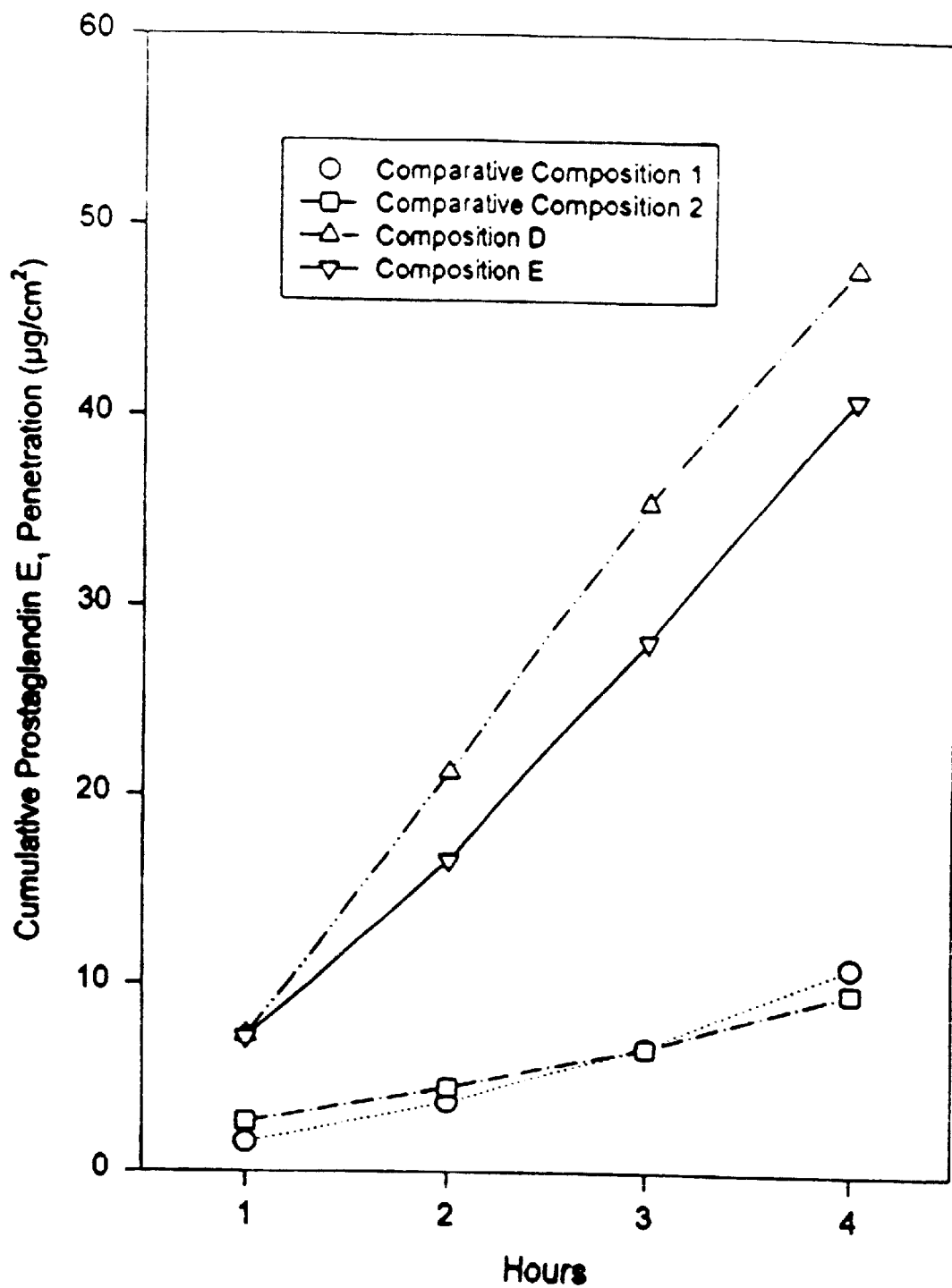
FIG. 4 is a comparison graph of the cumulative prostaglandin $E_1$ penetration through shed snake skin of two prostaglandin $E_1$ compositions prepared according to the present invention and two comparative compositions.

FIG. 3 is graph generated from the data presented in TABLE 1. Significantly, and well represented in graphical form, compositions according to the present invention deliver effective skin penetration relatively fast and at a sustained rate. As expected, cumulative penetration increases with increased prostaglandin $E_1$ loading of the source composition.

TABLE 2

Cumulative Prostaglandin $E_1$ Penetration ($\mu g/cm^2$)

| Hour | A | B | C | D | E | F | G |
|---|---|---|---|---|---|---|---|
| 1 | 1.96 | 3.37 | 5.47 | 7.20 | 7.09 | 10.38 | 3.03 |
| 2 | 5.49 | 9.72 | 18.06 | 21.26 | 16.6 | 25.03 | 8.17 |
| 3 | 11.25 | 18.18 | 30.34 | 35.53 | 28.24 | 42.18 | 12.93 |
| 4 | 13.98 | 23.48 | 38.49 | 47.98 | 41.1 | 52.13 | 18.71 |

To further assess the effectiveness of compositions according the present invention, comparative example compositions were prepared. A first comparative example (Comparative Example 1) was prepared with the same recipe as Compositions D and E except that the DDAIP penetration enhancer was omitted. For A second comparative example (Comparative Example 2), the DDAIP was again omitted, but the level of ethanol was increased a corresponding amount. The specific ingredients used are listed in TABLE 3, below.

TABLE 3

Comparative Examples

| Ingredient (wt %) | | Comparative Composition 1 | Comparative Composition 2 |
|---|---|---|---|
| Part A: | prehydrated locust bean gum | 3 | 3 |
| | water/buffer (pH 5.5) | 86 | 81 |
| | sucrose stearate | 0.5 | 0.5 |
| Part B: | prostaglandin $E_1$ | 0.4 | 0.4 |
| | ethanol | 5 | 10 |
| | ethyl laurate | 5 | 5 |

The penetration of prostaglandin $E_1$ from was evaluated according to the technique described in Example 1. The results are presented in TABLE 4, below.

TABLE 4

Comparative Examples
Cumulative Prostaglandin $E_1$ Penetration ($\mu g/cm^2$)

| Hour | Comparative Composition 1 | Comparative Composition 2 |
|---|---|---|
| 1 | 2.64 | 1.55 |
| 2 | 4.46 | 3.69 |
| 3 | 6.59 | 6.63 |
| 4 | 9.67 | 11.05 |

The data of TABLE 4 are compared graphically to the example compositions having the same prostaglandin $E_1$ loading, Compositions D and E. The penetration data demonstrate that compositions according to the present invention benefit greatly from the presence of the DDAIP penetration enhancer.

EXAMPLE 9

Single Use Double Blind and Open Label Clinical Trials

The safety and efficacy of a 0.4% prostaglandin $E_1$ (prostaglandin $E_1$ or alprostadil) topical composition (composition D of Example 4 and Table 1, above) was evaluated in a total of 143 men at three study sites. This study consisted of a double-blind, placebo controlled and cross-over portion and an open-label portion.

The double-blind placebo controlled portion of the study entered and completed 64 men (Table 5, below). Seventy-nine (79) men entered and completed the open-label portion of the study (Table 5, below). With the results of detailed statistical analyses on this study are outlined in the attached report, summarized below are discussions on the results of the clinical studies.

Inclusion Criteria

1. Males, ages 21–70 years, inclusive.

2. Documented history of erectile dysfunction, which is defined as the inability to achieve and maintain an erection of sufficient rigidity for sexual intercourse due to psychogenic, neurogenic or vasculogenic, causes during the previous 6 months. This includes patients who may still have some erections sufficient for intercourse but not consistently, which is the typical complaint of the age onset, mild to moderate impotent man. The diagnosis of erectile dysfunction will be based on medical history and physical examination.

Exclusion Criteria

1. History of urethral stricture or obstruction
2. Any combination of findings from history, physical examination or screening studies which indicate pre-existing impairment of heart, liver and/or kidney function (such as congestive heart failure, unstable angina or recent acute myocardial infarction, uncontrolled diabetes, for erectile dysfunction of hormonal origin) which in the investigator's opinion could influence the outcome of the study.
3. History of penile surgery, including penile implant, prostatectomy or cancer of the prostate, penile trauma including paraplegia or quadriplegia.
4. Any condition which might predispose towards priapism, such as sickle cell anemia, multiple myeloma, or leukemia.
5. Hypertension, (sitting diastolic pressure >90 or systolic >150) requiring treatment with other than angiotensin converting enzyme inhibitors (ACE inhibitors).
6. Presence of a sexually transmitted disease as determined by physical examination.
7. Use of a cavernosal injection or external erectile device within 4 weeks prior to entering into this study.
8. Peyronie's Disease or any palpable fibrous scar or plaque on the penis, evidence of curvature during tumescence and rigidity stimulation or an anomaly of the penis skin or mucosa of the glans.
9. Any concomitant medication which are known to interfere with sexual activity such as antidepressants, some antihypertensives, sedatives hormones and some allergy medications.
10. Received any investigational treatment within 30 days of entering into this study.
11. Inability or unwillingness to give informed consent.

The patient population in this study consisted of men in the age range of 49–70 years old.

TABLE 5

Patient Enrollment by Study Sites

| Portion | Patients Enrolled On Study Sites | | | |
|---|---|---|---|---|
| | No. 1 | No. 2 | No. 3 | Total |
| Double-Blind | 30 | 34 | 0 | 64 |
| Open Label | 32 | 8 | 39 | 79 |

Clinical efficacy was evaluated from patient history and patient evaluation questionnaires both before and after medication using a six-point classification scale (Table 6). Each patient was given one (1) placebo and one (1) active dose in a crossover manner with a 5 to 7 day wash-off period in the double-blind portion of the study. In the open-label portion the patients were given only one (1) active dose. The clinical supply was packaged in single-dose containers each containing 250 mg (net weight) of cream and 1.0 mg prostaglandin $E_1$.

The efficacy response rate was determined as the number of men that had erections sufficient for intercourse out of the total number of men. To be considered a success, a score of 8 to 10 must be achieved after administration of the dose or the patient must have had intercourse.

Statistical analysis compared before and after response scores using a paired t-test. A statistically significant difference ($P<0.001$) between all before and after dosing scores was found for each group of patients receiving active medication whether in the double-blind portion of the study or the open label portion of the study. Also, a statistically significance was seen between the active and placebo groups per study site.

TABLE 6

Six-Point Classification Scale for Assessing the Severity of Male Erectile Dysfunction (Impotence)

| Classification | Definition |
|---|---|
| 0 | Severe impotence with no function |
| 2 | Severe impotence with very little function |
| 4 | Severe impotence with some function |
| 6 | Mild to moderate impotence |
| 8 | Not impotent but has some loss of function |
| 10 | Not impotent with full function |

TABLE 7

Patient Enrollment by Impotence Classification

| | Severe | Mild to Moderate | Not Impotent | |
|---|---|---|---|---|
| Double-Blind | 39 | 25 | 0 | 64 |
| Open Label | 63 | 16 | 0 | 79 |
| Total Patients | 102 | 41 | 0 | 143 |

The topical prostaglandin $E_1$ composition was be safe and effective in impotent men with the to severe impotence. The efficacy rate was 64.7% (66/102 patients) in severely impotent men and 100% (41/41 patients) in mild to moderately impotent men. the overall clinical efficacy rate for the study is 74.8% (107/143 patients) as shown in Table 8, below.

TABLE 8

Overall Clinical Efficacy Rates

| | Double-Blind Portion | Open-Label Portion | Combined Overall Rate |
|---|---|---|---|
| Placebo | 4.7% (3/64) | — | 4.7% (3/64) |
| Active | 87.5% (56/64) P<0.001 | 64.6% (51/79) | 74.8% (107/143) P<0.001 |

The prostaglandin $E_1$ topical composition was extremely effective (100%) in the mild to moderate impotent patient population. The mild to moderate impotence class is the most prevalent class and is estimated to represent 70% of all erectile dysfunction complaints. The product was also very effective (64.7%) in the severely impotent study population.

A placebo efficacy response was seen in only 3 of 64 (4.7%) patients studied in the double-blind portion of the study. This is far below the expected rate of approximately 10% as reported in other clinical studies. This low rate is perhaps due to the fact that the majority (63%) of the patients enrolled in the double-blind portion of the study were classified with severe impotence. While 17 of 64 (26.6%) patients showed improvement with the placebo, only three (3) of those patients had sufficient improvement to be assessed as efficacious (8 or 10 on the classification scale).

TABLE 9

Clinical Efficacy Rates by Impotence Classification

| Portion | | Study Sites | | | Combined Efficacy |
|---|---|---|---|---|---|
| | | No. 1 | No. 2 | No. 3 | |
| Severely Impotent | Double-Blind | 85.7% (24/28) | 63.6% (7/11) | No Patients Entered | 79.5% (31/39) |
| | Open Label | 72.2% (13/18) | 33.3% (2/6) | 51.3% (20/39) | 55.6% (35/63) |
| Mild to Moderate Impotence | Double-Blind | 100% (2/2) | 100% (23/23) | No Patients Entered | 100% (25/25) |
| | Open Label | 100% ((14/14) | 100% (2/2) | No Patients Entered | 100% (16/16) |

The open label efficacy rate was lower than the double-blind efficacy rate (Table 9). This was primarily due to the enrollment of a relatively high number of severely impotent men in the open-label portion of the study as compared to the double-blind portion. (Table 8) Of the men enrolled in the open label portion of the study, 79.7% (63/79) were assessed as severely impotent while only 60.9% (39/64) were assessed as severely impotent on entering the double-blind portion. The efficacy rate among the severely impotent population is expected to be lower because by definition these men have little or no function. Practically, it is expected to be more difficult to move the impotence classification from 0, 2 or 4 up to 8 or 10. While most of the severely impotent men showed significant improvement, 36 men (36/102 or 35.3%) did not have sufficient improvement to be classified as efficacious.

Adverse events observed in this study were mild transient burning or tingling at the application site. No systemic toxic side effects were observed. Also, none of the spouses involved in the studies reported adverse events. None of the patients dropped out of the study or were lost to follow-up

EXAMPLE 10

Multiple Use Open Label Clinical Trial

The safety and efficacy of a 0.4% prostaglandin $E_1$ topical composition (composition D of Example 4 and Table 1, above) was evaluated in an additional study of a total of 56 men at three study sites. Fifty-six (56) male patients with organic erectile dysfunction entered and completed the study. Patients were classified into groups based on their responses to the International Index of Erectile Dysfunction (IIEF) and the pre dose Sexual Encounter Profile (SEP). Forty-nine (49) patients were classified as having mild to moderate erectile dysfunction and 7 patients were classified as having severe erectile dysfunction. Each patient was asked to use from 3 to 10 doses of medication over a four week period in a multiple use, in-home study. The overall efficacy rate for the mild to moderate group was 75%. The results of this study were consistent with the combined overall efficacy rate reported above in Example 9. None of the patients dropped out of this multiple use study and no severe adverse events were noted.

Inclusion Criteria

1. Males, ages 21–70 years, inclusive.

2. Documented history of erectile dysfunction, which is defined as the inability to achieve and maintain an erection of sufficient rigidity for sexual intercourse due to psychogenic, neurogenic or vasculogenic, causes during the previous 6 months. This includes patients who may still have some erections sufficient for intercourse but not consistently, which is the typical complaint of the age onset, mild to moderate impotent man. The diagnosis of erectile dysfunction will be based on medical history and physical examination.

Exclusion Criteria

1. History of urethral stricture or obstruction.

2. Any combination of findings from history, physical examination or screening studies which indicate pre-existing impairment of heart, liver and/or kidney function (such-as congestive heart failure, unstable angina or recent acute myocardial infarction, uncontrolled diabetes, for erectile dysfunction of hormonal origin) which in the investigator's opinion could influence the outcome of the study.

3. History of penile surgery, including penile implant, prostatectomy or cancer of the prostate, penile trauma including paraplegia or quadriplegia.

4. Any condition which might predispose towards priapism, such as sickle cell anemia, multiple myeloma, or leukemia.

5. Hypertension, (sitting diastolic pressure >90 or systolic >150) requiring treatment with other than angiotensin converting enzyme inhibitors (ACE inhibitors).

6. Presence of a sexually transmitted disease as determined by physical examination.

7. Use of a cavernosal injection or external erectile device within 4 weeks prior to entering into this study.

8. Peyronie's Disease or any palpable fibrous scar or plaque on the penis, evidence of curvature during tumescence and rigidity stimulation or an anomaly of the penis skin or mucosa of the glans.

9. Any concomitant medication which are known to interfere with sexual activity such as antidepressants, some antihypertensives, sedatives hormones and some allergy medications.

10. Received any investigational treatment within 30 days of entering into this study.

11. Inability or unwillingness to give informed consent.

The patient population in this study consisted of men in the age range of 49–70.

TABLE 10

Patient Enrollment by Study Sites

| Patients Enrolled On Study Sites | | | |
|---|---|---|---|
| No. 1 | No. 2 | No. 3 | Total |
| 22 | 13 | 21 | 56 |

Clinical efficacy was evaluated from patient history and patient evaluation questionnaires both before and after medication using the International Index of Erectile Function (Table 11) and the Sexual Encounter Profile (SEP) six-point classification scale Table 12). Each patient was given 10 active doses and asked to take the medication home and attempt intercourse as many times as possible over a 4 week period. The medication was packaged in a specially designed single dose applicator.

TABLE 11

International Index of Erectile Function

| Classification | Definition |
|---|---|
| <12 | Severe impotence with no function |
| 12–18 | Mild Impotence with very little function |
| 18–24 | Moderate Impotence with some function |
| 24+ | No dysfunction |

TABLE 12

Sexual Encounter Profile (SEP): Six-Point Classification Scale for Assessing the Severity of Male Erectile Dysfunction (Impotence)

| Classification | Definition |
|---|---|
| 0 | Severe impotence with no function |
| 2 | Moderate Impotence with very little function |
| 4 | Moderate Impotence with some function |
| 6 | Mild Impotence |
| 8 | Not impotent but has some loss of function |
| 10 | Not impotent with full function |

The efficacy response rate was determined as the number of intercourse successes out of the total number of intercourse attempts. To be considered a success, a SEP score of 8 to 10 must be achieved after administration of the dose or the patient must have had satistory sexual intercourse. Statistical analysis compared before and after respon se scores using Chi Square statistics. A statistically significant difference ($P<0.001$) between before and after dosing scores was found for each group of patients receiving active medication.

TABLE 13

Patient Enrollment by Impotence Classification

| | Severe | Mild to Moderate | Total |
|---|---|---|---|
| Patients | 7 | 49 | 56 |

TABLE 14

Efficacy per Patient Group

| | Efficacy by Patients | Efficacy by Attempts |
|---|---|---|
| Mild to Moderate | 36/49 (74%) | 178/239 (75%) |
| Severe | 4/7 (57%) | 16/36 (44%) |

As previously discussed, the prostaglandin $E_1$ topical composition was extremely effective (75%) in the mild to moderate impotent patient population. The mild to moderate impotence class is the most prevalent is class and is estimated to represent 70% of all erectile dysfunction complaints. The product was less effective (44%) in the severely impotent study population, however, there was a statistically significant difference between the before and after treatment scores in this group. Even though all of the men in the severe group were totally without any erectile function before the study, 4 of the 7 men (57%) had successful intercourse from at least 3 out of the 10 doses.

Adverse events observed in this study were mild transient burning or tingling at the application site. No systemic toxic side effects were observed. Also, none of the spouses involved in the studies reported adverse events. None of the patients dropped out of the study or were lost to follow-up. The results of this clinical indicate the use of the prostaglandin $E_1$ 0.4% topical composition of the present invention for the treatment of mild, moderate to severe impotence is safe and efficacious.

The foregoing specification is intended as illustrative and is not to be taken as limiting. Still other variations within the spirit and the scope of the invention are possible and will readily present themselves to those skilled in the art.

We claim:

1. A method of treating erectile dysfunction in a patient needing such treatment comprising:
   placing in the fossa navicularis of the patient an effective erection-inducing amount of a prostaglandin E1 composition comprising prostaglandin $E_1$;
   a skin penetration enhancer which is a member of the group consisting of an alkyl-2-(N,N-disubstituted amino)-alkanoate, an (N,N-disubstituted)-alkanol alkanoate, pharmaceutically acceptable salts thereof and a mixture thereof;
   a polysaccharide gum;
   a lipophilic compound which is a member of the group consisting of an aliphatic $C_1$ to $C_8$ alcohol, an aliphatic $C_8$ to $C_{30}$ ester, and a mixture thereof; and
   an acidic buffer system.

2. The method of claim 1 wherein at least 50% of the amount of the prostaglandin E1 composition is retained in the fossa navicularis.

3. The method of claim 1 wherein at least 80% of the amount of the prostaglandin E1 composition is retained in the fossa navicularis.

4. The method of claim 1 wherein the prostaglandin E1 composition is placed in the fossa navicularis using an applicator that ends within the limits of the fossa navicularis when placing the composition.

5. The method of claim 4 wherein the applicator extends less than one centimeter into the penis.

6. The method in accordance with claim 1 wherein said penetration enhancer is a alkyl-2-(N,N-disubstituted amino)-alkanoate represented by the formula:

$$H_3C-(CH_2)_{\overline{n}}-\underset{R_4}{\overset{R_3}{\underset{|}{\overset{|}{C}}}}-O-\underset{R}{\overset{O}{\overset{||}{C}}}-\underset{R_2}{\overset{H}{\underset{|}{\overset{|}{C}}}}-N\overset{R_1}{\underset{R_2}{\diagdown}}$$

wherein n is an integer having a value in the range of about 4 to about 18; R is a member of the group consisting of hydrogen, $C_1$ to $C_7$ alkyl, benzyl and phenyl; $R_1$ and $R_2$ are members of the group consisting of hydrogen and $C_1$ to $C_7$ alkyl; and $R_3$ and $R_4$ are members of the group consisting of hydrogen, methyl and ethyl.

7. The method in accordance with claim 1 wherein said penetration enhancer is a $C_4$ to $C_{18}$ alkyl (N,N-disubstituted amino)-acetate.

8. The method in accordance with claim 1 wherein said penetration enhancer is a dodecyl (N,N-dimethylamino)-acetate.

9. The method in accordance with claim 1 wherein said penetration enhancer is a dodecyl 2-(N,N-dimethylamino)-propionate.

10. The method in accordance with claim 1 wherein said penetration enhancer is an (N,N-disubstituted amino)-alkanol alkanoate represented by the formula:

$$H_3C-\left[\begin{array}{c}R_3\\|\\C\\|\\R_4\end{array}\right]_n-\overset{O}{\overset{||}{C}}-O-\left[\begin{array}{cc}R_5\\|\\C\\|\\R_6\end{array}\begin{array}{c}R_7\\|\\C\\|\\R_8\end{array}\right]_y-N\overset{R_1}{\underset{R_2}{\diagdown}}$$

wherein n is an integer having a value in the range of about 5 to about 18; y is an integer having a value in the range of 0 to about 5; and $R_1$, $R_2$, $R_3$, $R_4$, $R_5$, $R_6$, and $R_7$ are members of the group consisting of hydrogen, $C_1$ to $C_8$ alkyl, and $C_1$ to $C_8$ aryl; and $R_8$ is a member of the group consisting of hydrogen, hydroxyl, $C_1$ to $C_8$ alkyl, and $C_1$ to $C_8$ aryl.

11. The method in accordance with claim 1 wherein said penetration enhancer is a $C_5$ to $C_{18}$ carboxylic acid ester.

12. The method in accordance with claim 1 wherein said penetration enhancer is a 1-(N,N-dimethylamino)-2-propanol dodecanoate.

13. The method in accordance with claim 1 wherein said penetration enhancer is a 1-(N,N-dimethylamino)-2-propanol myristate.

14. The method in accordance with claim 1 wherein said penetration enhancer is a 1-(N,N-dimethylamino)-2-propanol oleate.

15. The method in accordance with claim 1 wherein said polysaccharide gum is a galactomannan gum.

16. The method in accordance with claim 15 wherein said galactomannan gum is a locust bean gum.

17. The method in accordance with claim 15 wherein said galactomannan gum is a guar gum.

18. The method in accordance with claim 1 wherein said lipophilic compound is ethanol.

19. The method in accordance with claim 1 wherein said lipophilic compound is a polyol aliphatic alcohol.

20. The method in accordance with claim 1 wherein said lipophilic compound is isopropyl myristate.

21. The method in accordance with claim 1 wherein said lipophilic compound is ethyl laurate.

22. The method in accordance with claim 1 wherein said lipophilic compound is a mixture of ethanol and isopropyl myristate.

23. The method in accordance with claim 1 wherein said lipophilic compound is a mixture of ethanol and ethyl laurate.

24. The method in accordance with claim 1 wherein said acidic buffer system is capable of providing a buffered pH value for said composition in the range of about 3 to about 7.4.

25. The method in accordance with claim 1 wherein said penetration enhancer is a dodecyl 2-(N,N-dimethylamino)-propionate, said polysaccharide gum is a locust bean gum, and said lipophilic compound is a mixture of ethanol and ethyl laurate.

26. A method in accordance with claim 1, which contains 0.5 to 5 weight percent locust bean gum, 0.5 to 25 weight percent dodecyl 2-(N,N-dimethylamino)-propionate, 0.5 to 80 weight percent ethanol, and 0.5 to 80 weight percent isopropyl myristate, based on the total weight of the composition.

27. A method in accordance with claim 1, which contains 0.5 to 5 weight percent locust bean gum, 0.5 to 5 weight percent dodecyl 2-(N,N-dimethylamino)-propionate, 0.5 to 25 weight percent ethanol, and 0.5 to 25 weight percent ethyl laurate, based on the total weight of the composition.

28. A method in accordance with claim 1, which further contains an emulsifier.

29. A method in accordance with claim 28 wherein said emulsifier is an sucrose ester.

30. A method in accordance with claim 28 wherein said emulsifier is sucrose stearate.

31. A method of treating erectile dysfunction in a patient needing such treatment comprising:

placing in the fossa navicularis of the patient an effective erection-inducing amount of a prostaglandin E1 composition comprising prostaglandin $E_1$;

a skin penetration enhancer which is a member of the group consisting of an alkyl-2-(N,N-disubstituted amino)-alkanoate, an (N,N-disubstituted)-alkanol alkanoate, and a mixture thereof;

a polyacrylic acid polymer;

a lipophilic compound which is a member of the group consisting of an aliphatic $C_1$ to $C_8$ alcohol, an aliphatic $C_8$ to $C_{30}$ ester, and a mixture thereof; and an acidic buffer system.

32. A method in accordance with claim 31 wherein said polyacrylic acid polymer is a carbomer.

* * * * *

UNITED STATES PATENT AND TRADEMARK OFFICE
CERTIFICATE OF CORRECTION

PATENT NO. : 6,323,241 B1
DATED : November 27, 2001
INVENTOR(S) : J.L. Yeager, N. Buyuktimkin and S. Buyuktimkin It is certified that error appears in the above-identified patent and that said Letters Patent is hereby corrected as shown below:

Column 5,
Line 64, please insert a space between "(Cowper's glands)" and "can".

Column 6,
Line 4, please delete "lo".

Column 10,
Line 15, please delete "$_\beta$" and insert -- $\beta$ --. Please delete "⌐" and insert -- → --
Line 16, please delete "$_\alpha$" and insert -- $\alpha$ --. Please delete "⌐" and insert -- → --

Column 21,
Line 17, please delete "Table 12)." and insert -- (Table 12). --

Signed and Sealed this

Twenty-third Day of April, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO.    : 6,323,241 B1
DATED         : November 27, 2001
INVENTOR(S)   : James L. Yeager, Nadir Büyüktimkin and Servet Büyüktimkin It is certified that error appears in the above-identified patent and that said Letters Patent is hereby corrected as shown below:

<u>Column 22,</u>
Line 45, please delete "(N, N-disubstituted)" and insert -- (N, N-disubstitated) amino) --.

<u>Column 24,</u>
Line 47, please delete "(N, N-disubstituted)" and insert -- (N, N-disubstitated) amino) --.

Signed and Sealed this

Twenty-sixth Day of August, 2003

JAMES E. ROGAN
*Director of the United States Patent and Trademark Office*